United States Patent [19]

Tsau et al.

[11] Patent Number: 4,971,791
[45] Date of Patent: Nov. 20, 1990

[54] TASTE MASKING COMPOSITIONS

[75] Inventors: Josef H. Tsau, Skokie; Nalinkant C. Damani, Arlington Heights, both of Ill.

[73] Assignee: The Procter & Gamble Company, Cincinnati, Ohio

[21] Appl. No.: 517,965

[22] Filed: May 1, 1990

Related U.S. Application Data

[63] Continuation of Ser. No. 402,987, Sep. 1, 1989, abandoned, which is a continuation of Ser. No. 287,246, Dec. 20, 1988, abandoned, which is a continuation of Ser. No. 170,086, Mar. 10, 1988, abandoned, which is a continuation of Ser. No. 768,981, Aug. 26, 1985, abandoned.

[51] Int. Cl.$^5$ .................. A61K 9/26; A61K 31/78
[52] U.S. Cl. ........................................... 424/81; 424/441
[58] Field of Search .................. 424/81, 441

[56] References Cited

U.S. PATENT DOCUMENTS

| | | | |
|---|---|---|---|
| 3,594,470 | 7/1971 | Borodkin et al. | 424/32 |
| 3,608,063 | 9/1971 | Banker | 424/81 |
| 3,629,392 | 12/1971 | Banker | 424/81 |
| 3,919,436 | 11/1975 | Takabe et al. | 424/497 |
| 3,981,984 | 9/1976 | Signorino | 424/482 |
| 4,060,598 | 11/1977 | Groppenbacher et al. | 424/482 |
| 4,101,651 | 7/1978 | Kobayashi et al. | 424/78 |
| 4,140,756 | 2/1979 | Gallian | 424/482 |
| 4,178,361 | 12/1979 | Cohen et al. | 424/81 |
| 4,330,338 | 5/1982 | Banker | 424/482 |
| 4,542,011 | 9/1985 | Glelxner | 424/493 |
| 4,556,552 | 12/1985 | Porter et al. | 424/482 |
| 4,575,539 | 3/1986 | DeCrosta et al. | 424/81 |
| 4,576,646 | 3/1986 | Brancu et al. | 424/494 |
| 4,649,041 | 3/1987 | Peters et al. | 424/484 |
| 4,656,027 | 4/1987 | Astia Lakemedal | 424/495 |
| 4,666,703 | 5/1987 | Kopf | 424/470 |
| 4,708,867 | 11/1987 | Hsiao | 424/80 |
| 4,710,384 | 12/1987 | Rotman | 424/465 |
| 4,749,575 | 6/1988 | Rotman | 424/441 |
| 4,760,093 | 7/1988 | Blank et al. | 424/81 |
| 4,800,087 | 1/1989 | Mehtz et al. | 424/497 |
| 4,808,411 | 2/1989 | Lu et al. | 424/441 |
| 4,847,090 | 7/1989 | Della Posta | 424/440 |
| 4,929,448 | 5/1990 | Ibsen | 424/489 |

FOREIGN PATENT DOCUMENTS

| | | |
|---|---|---|
| 212641 | 3/1987 | European Pat. Off. |
| 219458 | 4/1987 | European Pat. Off. |
| 247634 | 12/1987 | European Pat. Off. |
| 3601002 | 7/1986 | Fed. Rep. of Germany |
| 2476485 | 8/1981 | France |
| 664284 | 2/1988 | Switzerland |

OTHER PUBLICATIONS

Damani et al., CA-107: 83915d (1987) of EPO 212641, Mar. 4, 1987, 1981.
Ghebre-Sellasjie, CA-107: 83817y (1987) of Int. J. Pharm. 37(3): 211-218 (1987).
Ghebe-Sellasjie, CA-105: 134641q (1986) of DE 3601002, Jul. 31, 1986, 22 pp.
Ghebe-Sellasjie, CA-105: 102472j (1986) of Int. J. Pharm. 31(1-2): 43-54 (1986).
Peters et al., CA-107: 161706c (1987) of U.S. 4,649,041, Mar. 10, 1987.
Vincze et al., CA-110: 179515m (1988) of Switz 664284, Feb. 29, 1988, 4 pp.
Mehta, CA-110: 44965n (1988) of PCT WO 88/3795, Jun. 2, 1988, 28 pp.
Blank, CA-109: 237034w (1988) of EPO 266113, May 4, 1988, 8 pp.
Kauro, CA-109: 79623f (1988).
Hsiao, CA-226864v (1987) of U.S. 4,708,867, Nov. 24, 1987.
Ghebre-Sellasjie; CA-108-62505A, 1987 of EP 247634.
Ser. C-96 40911m 1981 of Fr. 2476485, Aug. 28, 1981.

Primary Examiner—Shep K. Rose
Attorney, Agent, or Firm—Douglas C. Mohl; Kim William Zerby; Jack D. Schaeffer

[57] ABSTRACT

This disclosure relates to drug-polymer matrix compositions comprising an active ingredient having an amine or amido group and a pharmaceutically acceptable copolymer having a plurality of carboxylic acid and ester groups wherein the matrix dissociates in a media having a pH of less than 4, thereby releasing the active ingredient into the media.

1 Claim, No Drawings

TASTE MASKING COMPOSITIONS

This is a continuation of application Ser. No. 402,987, filed on Sept. 1, 1989, which is a continuation of application Ser. No. 287,246, filed on Dec. 20, 1988, which is a continuation of application Ser. No. 170,086, filed on Mar. 10, 1988, which is a continuation of application Ser. No. 170,086, filed on Mar. 10, 1988, which is a continuation of application Ser. No. 768,981, filed Aug. 26, 1985, all of which are now abandoned.

The present invention relates to drug-polymer compositions effective in masking the taste of bitter drugs. The invention further relates to methods for preparing such compositions.

BACKGROUND OF THE INVENTION

Chewable and lozenge dosage forms are preferred by individuals who have difficulty swallowing tablets and capsules. Frequently, sweeteners and flavors, along with diluting agents have been utilized as fillers in an attempt to minimize unpleasant or bitter taste of pharmaceutical active ingredient.

Many drugs, in particular drugs containing amine or amido groups or salts thereof, often have a strong bitter taste. Without proper taste-masking, such drugs cannot be adapted into acceptable tasting chewables and lozenges. One example of a bitter amino drug is dimenhydrinate. In addition to its bitter taste, dimenhydrinate produces a numbing effect that is equally as unpleasant.

Taste-masking techniques using various sweeteners, amino acids, acids, flavors and adsorbents have been unsuccessful in masking the taste of dimenhydrinate or if the taste is somewhat masked, the resulting product is therapeutically ineffective. One method involves the enteric coating of bitter tasting drugs with various copolymers. However, enteric coating has been ineffective. The coating of fine particle materials is usually unsuccessful and the coatings of granular particles are readily ruptured by chewing and compression. In addition, most coatings do not have an acceptable in vivo drug releasing mechanism.

Cation-exchange resins have been used to adsorb amine drugs for sustained release action and taste-masking. The widely used cation-exchange resins are polysulfonic acid and polycarboxylic acid polymers. In addition rice endosperm has been used to mask the taste of drugs utilizing its properties of stickiness and insolubility to physically entrap the drug molecules. However, neither technique has been effective in masking the bitter taste or numbing effect associated with dimenhydrinate.

SUMMARY OF THE INVENTION

The present invention relates to a porous drug-polymer matrix comprising an active ingredient having an amine or amido groups or salt thereof and a pharmaceutically acceptable copolymer having a plurality of carboxylic acid and ester groups wherein the matrix dissociates in a media having a pH less than 4, thereby releasing the active ingredient into the media. The porous drug-polymer matrix of the present invention is formed by adsorbing one or more active ingredients and a pharmaceutically acceptable copolymer, or mixture of copolymers, in the presence of a solvent and then removing the solvent from the mixture to yield a porous matrix. The porous drug-polymer matrix of the present invention is effective in masking the taste of an active ingredient and releasing the active ingredient in the stomach. The present invention further relates to a method for masking the taste of an active ingredient and to a method for preparing such compositions.

DETAILED DESCRIPTION OF THE INVENTION

In accordance with the present invention, the taste of an active ingredient is masked by admixing an active ingredient and a pharaceutically acceptable copolymer in the presence of a solvent and then removing the solvent to yield a porous drug-polymer matrix. The porous matrix thus formed is readily distinguished from a product comprising an active ingredient enterically coated with a copolymer by the fact that at a pH of less than 4 the drug polymer matrix releases the active ingredient wherein an enterically coated active ingredient will only be significantly released in an alkaline media.

The copolymers effective in the compositions and methods of the present invention are pharmaceutically acceptable anionic copolymers capable of interacting with an active ingredient and form an a porous drug-polymer matrix. The copolymers utilized in the present invention include copolymers having a plurality of carboxylic acid and ester groups. Such groups are largely responsible for physical or chemical interactions with an active ingredient for effective taste masking properties. The preferred copolymers contain either a vinyl and acrylic acid and/or ester groups or carboxylic acid and/or ester groups. The specific copolymers are readily ascertained by one of ordinary skill in the art. Generally, copolymers that are pharmaceutically acceptable in terms of safety and toxicity may be utilized to mask the taste of an active ingredient in accordance with the present invention. It is preferred that such copolymers be soluble in a solvent or a mixture of solvents. Such copolymers include polymeric or resinous substances such as: co-polymers of acrylic and substituted acrylic acids; cellulose esters; vinyl and substituted vinyl esters; polysulfonic acids, their esters and amides. Specific examples include naturally occurring materials such as shellac and zein and synthetic and semi-synthetic materials such as cellulose acetates. cellulose acetate phthallates, ethyl vinyl acetates and/or phthalates, polyvinyl acetates and/or phthalates, ethyl and/or methyl methacrylic acids, esters and co-polymers, hydroxy alkyl cellulose acetates and/or phthalates. Such compounds include commercially available materials sold under trade names such as Eudragit S (trademark of Rohm Pharma) and Phthalavin (trademark of Colorcon).

The active ingredients capable of forming a drug-polymer matrix with a copolymer include drugs having an amine or amido group capable of physically or chemically interacting with the carboxylic acid and esters thereof groups of the copolymer. As used herein the term "amine" functional group includes primary, secondary and tertiary amine groups. The term "amido functional group" refers to a

moiety. The type of interaction will vary depending upon the chemical structure of the active ingredient and copolymer. Depending on a given active ingredient, one or more of the physical or chemical interactions occur to provide the desirable taste masking effects The methods for preparing the porous drug-polymer matrix of the present ensures that physical effect, such as molecular inclusion adsorption and granulation are present to significantly reduce the rate of release of the active ingredient and thereby effectively reduce the bitter taste of the active ingredient in the mouth. Illustrative of such physical or chemical interactions include one or more of the following: partial molecular inclusion, hydrogen bonding, salt formation, ion-pair and complex formations, hydrogen-bonding and granulation. The particular type of interaction depends upon the specific active ingredient(s) and copolymer(s) utilized. Representative of active ingredients incorporated into the porous matrix in accordance with the present invention include, for example, alkaloids, amines and amphetamines, amides, aminophenols, imines, phenothizines pyridines, pyrimidines, sulfonic acids, sulfonamides, quinolines xanthines and acidic drugs. The quantity of active ingredient in the drug-polymer matrix of the present invention is in a dose effective for the treatment intended. Therapeutically effective doses of the active ingredient required to prevent or arrest the progress of the medical condition to be treated, are readily ascertained by one of ordinary skill in the art.

As previously noted, the compositions of the present invention may be prepared by mixing one or more active ingredients with an anionic copolymer or mixture of anionic copolymers in the presence of an appropriate solvent and then removing the solvent. Although not required, a plasticizer such as glycols, sorbitol, vegetable oil may be optionally added. The solvent or a mixture of solvents is added to thoroughly wet the mixture. Preferred solvents include pharmaceutically acceptable solvents wherein both the active ingredient and the copolymer are soluble or swellable. Pharmaceutically preferred solvents include ketones such as acetone, alcohols such as ethanol, esters such as ethyl acetate and their mixtures with or without water. Alternatively, a solution of either the active ingredient or copolymer is prepared in a solvent or a mixture of solvents and the solution is then combined with the remainding components. The solvent is then removed by conventional methods. Such methods include vacuum evaporation, tray drying, spray drying, drum or belt film drying. Elevated temperatures may be employed provided the temperature at which the solvent is removed does not cause the active ingredient or copolymer to decompose. It is preferred that the solvent be removed under vacuum while heating in order to yield a matrix having a porous structure and thereby enhances the release of the active ingredient in acidic media. The porous matrix is preferably ground to the desired granular size and is then utilized in the preparation of tablets, chewing gum, wafers, candy and like.

The ratio of active ingredient to copolymer is dependent upon the degree to which the taste is to be masked. An effective taste masking amount of copolymer is employed An effective taste masking amount of the copolymer refers to an amount of copolymer sufficient to mask the taste of an active ingredient. Generally a ratio of 1:1 by weight of active ingredient: copolymer is preferred. It is ascertained by one of ordinary skill in the art that the ratio can be optimized by studying the taste and the in vitro release profiles of the active ingredient.

The quantity of solvent employed is not critical and is determined by the method selected for solvent removal. For example, if a film drying process is selected, it may be necessary to use more solvent to make the film prior to solvent removal. However, if vacuum tray drying process is employed, only a minimal amount of solvent is employed.

Extremely unpleasant tasting active ingredients such as quinine may require higher concentation of copolymer to obtain a desirable level of taste masking. However, this may delay the release of the active ingredient from the powdered drug-polymer matrix. It is known that artificial sweeteners such as aspartame, cyclamate, saccharin, will reduce the bitter taste of certain drugs. Small amounts of such sweetener(s) and/or a flavoring agent(s) can be incorporated during the process of preparing the porous drug polymer matrix to optimize the taste masking effect.

The copolymer employed in the present invention function as a carrier of the active ingredient, thus preventing the release of the active ingredient only while the matrix is in the mouth, but permitting release of the active ingredient in the stomach, thereby effectively masking the taste of the active ingredient. Thus, in theory and practice, the methods of the present invention are significantly different from a classical enteric coating process. In accordance with enteric coating techniques, an active ingredient or a formulated tablet containing the active ingredient is completely coated by a film of a polymer. The resulting polymeric film is insoluble and non-diffusible to the active ingredient below the intestinal pH of about 1. In order for the enclosed active ingredient to be released, the external coating first must be dissolved or ruptured in an alkaline pH enviroment, namely that of intestine. Thus, an enterically coated active ingredient will not be released into the stomach wherein the pH is less than 5. Further, an enteric coating product must be kept intact and swallowed without breaking the coating. However, the porous drug-polymer matrix of the present invention is generally powdered and may be formulated into chewable tablets, chewy confectionery products and like without any adverse effects on the release of the active ingredient. The taste of the active ingredient in such formulated products, even when masticated during consumption, is not apparent.

The following Examples are intended to further illustrate the present invention and not to limit the invention in spirit or scope. In the Examples, all parts are parts by weight unless otherwise expressly set forth.

EXAMPLE 1

To a mixture of 0.05 g. of dimenhydrinate and 0.05 g. of polyvinylacetate phthalate is added 0.1 g. of a 1:1 ethyl alcohol:acetone mixture. The mixture was stirred and the ethyl alcohol:acetone was evaporated from the mixture at 60° C. under vacuum to yield a porous matrix. The matrix is granulated by passing the matrix through a sieve mesh #60. The granulated matrix is added to 0.5 g. of sorbitol, 0.1 g. of mannitol, 0.003 g. of magnesium stearate and q.s. color and flavor and the resulting mixture is compressed into a bitterless chewable tablet providing 50 mg. of dimenhydrinate for control of motion sickness.

EXAMPLE 2

To a mixture of 0.015 g. of dextromethorphan hydrobromide, 0.0225 g. of Eudragit L-100 and 0.0075 g. of L-aspartylphenylalaninemethylester is added 0.045 g. of ethyl alcohol. The ethyl alcohol is evaporated from the mixture at 60° C. under vacuum to yield a porous matrix. The matrix is powdered by passing the matrix through a sieve mesh #60. The powdered matrix is added to 0.25 g. of mannitol, 0.25 g. of sugar, 0.005 g. of calcium stearate and q.s. color and flavor and the resulting mixture is compressed into a bitterless tablet providing 0.015 g. of dextromethorphan for control of cough due to cold or allergy.

EXAMPLE 3

To 0.656 g. a mixture of a 1:1:0.1 mixture of acetaminophen, Eudragit S-100 and calcium saccharin was added 656 ml. of ethyl alcohol. The mixture was stirred and the ethyl alcohol was evaporated from the mixture at 60° C. under vacuum to yield a porous matrix. The matrix is granulated by passing the matrix through a sieve mesh #60. The granulated matrix is added to 0.3 g. sugar, 0.18 g. of sodium starch glycolate, 0.005 g. of magnesium stearate and q.s. color and flavor and the resulting mixture is compressed into a bitterless chewable tablet providing 0.325 g. of acetaminophen for relieving aches, pain and fever.

EXAMPLE 4

To a mixture of 0.0125 g. of pseudoephedrine, 0.0125 g. of dextromethorphan, 0.001 g. of chlorpheniramine, 0.044 g. of Eudragit S-100 and 0.010 g. of aspartame is added 0.15 g. of ethyl alcohol. The mixture is stirred and the ethyl alcohol is evaporated from the mixture at 60° C. under vacuum to yield a porous matrix. The matrix is granulated by passing the matrix through a sieve mesh #60. The granulated matrix is incorporated into a chewy candy base containing sugar, corn syrup solids, gelatin, dextrin, partially hydrogenated vegetable oil, citric acid, menthol and lemon-peppermint flavor, to yield bitterless sour-menthol and chewy squares providing effective relief of cough, cold and allergy symptoms.

EXAMPLE 5

To a mixture of 0.025 g. of phenylpropanolamine and 0.035 g. of cellulose acetate phthalate was added 60 ml. of ethyl alcohol. The mixture was stirred and the ethyl alcohol was evaporated from the mixture at 60° C. and under vacuum to yield a porous matrix. The matrix was granulated by passing the matrix through a sieve mesh #60. The granulated matrix was added to 1.2 g. sugar, 0.3 g. sorbitol, 0.06 g. dextrose and 0.003 g. peppermint flavor and the resulting mixture is formulated into a bitterless soft confectionary product for appetite control.

EXAMPLE 6

To a mixture of 15 g. of dimenhydrinate and 15 g. of Eudragit S-100 was added 30 ml. of ethyl alcohol. The mixture was stirred under gentle heat to yield a viscous mass which was thinly spread on a tray and dried at 70° C. under vacuum to yield a porous matrix. The matrix was granulated by passing the matrix through a sieve mesh #60. 100 mg. of the granulated matrix was added to a mixture of 0.3 g. sugar, 0.2 g. mannitol, 0.005 g. of magnesium stearate and q.s. color and flavor and the resulting mixture was compressed into a bitterless chewable tablet providing 0.05 g. of dimenhydrinate.

In vitro test conducted on a selected products produced in accordance with the methods of the present invention demonstrated that release of the active ingredient occurs at a pH of 1.

Although this invention has been described with respect to specific modification, the details thereof are not to be construed as limitations, for it will be apparent that various equivalents, changes and modifications may be restored and modification may be resorted to without departing from the spirit and scope thereof and it is understood that such equivalent embodiments are intended to be included therein.

What is claimed is:

1. A chewable drug polymer chewable matrix comprising bitter tasting dimenhydrinate taste masked with a pharmaceutically acceptable copolymer which is methyl methacrylic ester wherein the chewable matrix dissociates in a media having a pH less than 4, thereby releasing the taste masked bitter active ingredient into the media.

* * * * *